(12) United States Patent
Ofek et al.

(10) Patent No.: US 10,743,790 B2
(45) Date of Patent: Aug. 18, 2020

(54) SUBJECTIVE SIGNIFICANCE EVALUATION TOOL, BRAIN ACTIVITY BASED

(75) Inventors: Einat Ofek, Auckland (NZ); Hillel Pratt, Nofit (IL)

(73) Assignee: Einat Ofek, Yokneam (IL)

( * ) Notice: Subject to any disclaimer, the term of this patent is extended or adjusted under 35 U.S.C. 154(b) by 0 days.

(21) Appl. No.: 13/313,615

(22) Filed: Dec. 7, 2011

(65) Prior Publication Data
US 2012/0245474 A1 Sep. 27, 2012

Related U.S. Application Data

(63) Continuation of application No. 11/845,564, filed on Aug. 27, 2007, now abandoned.

(60) Provisional application No. 60/839,909, filed on Aug. 25, 2006.

(51) Int. Cl.
*A61B 5/0484* (2006.01)

(52) U.S. Cl.
CPC .................. *A61B 5/0484* (2013.01)

(58) Field of Classification Search
CPC .................................................. A61B 5/0484
USPC ......... 600/300, 301, 309, 544–545, 558–559
See application file for complete search history.

(56) References Cited

U.S. PATENT DOCUMENTS

| | | | | |
|---|---|---|---|---|
| 5,406,956 A | * | 4/1995 | Farwell | 600/544 |
| 7,580,742 B2 | * | 8/2009 | Tan et al. | 600/544 |
| 7,647,096 B2 | * | 1/2010 | Nowinski et al. | 600/544 |
| 2003/0004423 A1 | * | 1/2003 | Lavie et al. | 600/500 |
| 2007/0249914 A1 | * | 10/2007 | Cacioppo et al. | 600/300 |
| 2010/0042011 A1 | * | 2/2010 | Doidge et al. | 600/544 |

OTHER PUBLICATIONS

Esslen, et al., "Brain areas and time course of emotional processing," NeuroImage, vol. 21, Issue 4, Apr. 2004, pp. 1189-1203.*
Berlad, et al. "P300 in response to the subject's own name," Electroencephalography and clinical Neurophysiology 96: 472-474 (1995).*
Carretie, et al. "Automatic Attention to Emotional Stimuli: Neural Correlates," Human Brain Mapping 22:290-299 (2004).*
Attias, J., et al., Auditory event related potentials in chronic tinnitus patients with noise induced hearing loss, Hearing Research, 1993, p. 106-113, 71, Elsevier Science Publishers B.V.
Bar, Amir, et al., Evaluationof a Portable Device Based on Peripheral Arterial Tone for Unattended Home Sleep Studies, Chest Journal, 2003, p. 695-703, 123, 3.
Berland, I and Pratt H., P300 in response to subject's own name, Electroencephalography and clinical Neurophysiology, 1995, p. 472-474, 96, Elsevier Science Ireland Ltd.

(Continued)

*Primary Examiner* — Eric J Messersmith

(57) ABSTRACT

A method and system for determining the subjective state of mind of a human subject presented with a test audible or visual stimulus. An an electroencephalogram (EEG) recording unit is connected to the human subject, recording the subject's EEG when presented with one or more test stimuli. The recorded EEG signal is then transformed to a 3-D map in order to visualize the brain areas that were active when presenting the test stimuli. The given 3-D map of the test stimuli is then compared with reference 3-D maps of neutral and subjectively significant stimuli.

18 Claims, 12 Drawing Sheets
(10 of 12 Drawing Sheet(s) Filed in Color)

(56) References Cited

OTHER PUBLICATIONS

Blair, R.J.R., et al., Dissociable neural responses to facial expressions of sadness and anger, Brain, 1999, p. 883-893, 122, Oxford Univeristy Press.

Critchley, Hugo, Emotion and its disorders, British Medical Bulletin, 2003, p. 35-47, 65, The British Council.

Crosson, Bruce M., et al., Semantic monitoring of words with emotional connotation during fMRI: Contribution of anterior left frontal cortex, Journal of International Neuropsychological Society, 2002, p. 607-622, vol. 8, Issue 5.

Davidson, Richard J. and Irwin, William, The functional neuroanatomy of emotion and affective style, Trends in Cognitive Science, 1999, p. 11-21, vol. 3, No. 1.

Devinsky, Orrin, et al., Contributions of anterior cingulate cortex to behaviour, Brain, 1995, p. 279-306, 118, Oxford University Press.

Dietrich, Detlef E., et al., Differential Effects of Emotional Content on Event-Related Potentials in Word Recognition Memory, Neuropsychobiology, 2001, p. 96-101, 43.

Dvir, I., et al., Evidence for fractal correlation properties in variations of peripheral arterial tone during REM sleep, American Journal of Physiology—Heart and Circulatory Physiology, 2002, p. H434-H439, 283.

Elliott, Rebecca, et al., Selective attention to emotional stimuli in a verbal go/no-go task: an fMRI study, Brain Imaging, 2000, p. 1739-1744, vol. 11 (8).

Elliott, Rebecca, et al., The Neural Basis of Mood-Congruent Processing Biases in Depression, Arch Gen Psychiatry, 2002, p. 597-604, vol. 59.

Esslen, M., et al., Brain areas and time course of emotional processing, NeuroImage, 2004, p. 1189-1203, 21, Elsevier Inc.

Farwell, Laurence A. and Smith, Sharon S., Using Brain MERMER Testing to Detect Knowledge Despite Efforts to Conceal, Journal of Forensic Sciences, 2001, p. 135-143.

Ganis, G., et al., Neural Correlates of Different Types of Deception: An fMRI Investigation, Cerebral Cortex, 2003, p. 83-836, 13, Oxford University Press.

George, Mark S., et al., Brain Activity During Transient Sadness and Happiness in Healthy Women, American Journal of Psychiatry, 1995, p. 341-351, 152:3.

Gundel, Harald, et al., Functional Neuroanatomy of Grief: An fMRI Study, American Journal of Psychiatry, 2003, p. 1946-1953, 160:11.

Hamann, Stephan and Mao, Hui, Positive and negative emotional verbal stimuli elicit activity in the left amygdala, Brain Imaging, 2002, p. 15-19, vol. 13, No. 1, Lippincott Williams & Wilkins.

Imaizumi, Satoshi, et al., Vocal Identification of speaker and emotion activates different drain regions, NeuroReport, 1997, p. 2809-2812, 8, Rapid Science Publishers.

Jones, Barbara E., Arousal Systems, Frontiers in Bioscience, 2003, p. 438-451, 8.

Jones, Nancy Aaron and Fox, Nathan A., Electroencephalogram Asymmetry during Emotionally Evocative Films and Its Relation to Positive and Negative Affectivity, Brain and Cognition, 1992, p. 280-299, 20, Academic Press, Inc.

Kampe, Knut K.W., et al., "Hey John": Signals Conveying Communicative Intention toward the Self Activate Brain Regions Associated with "Mentalizing," Regardless of Modality, The Journal of Neuroscience, 2003, p. 5258-5263, 23 (12).

Kozel, Frank Andrew, et al., A Replication Study of the Neural Correlates of Deception, Behavioral Neuroscience, 2004, p. 852-856, vol. 118, No. 4.

Langleben, D.D., et al., Brain Activity during Simulated Deception: An Event-Related Functional Magnetic Resonance Study, NeuroImage, 2002, p. 727-732, 15, Elsevier Science (USA).

Maddock, Richard J. and Buonocore, Michael H., Psychiatry Research: Neuroimaging, 1997, p. 1-14, 75, Elsevier Science Ireland Ltd.

Maddock, Richard J., et al., Posterior Cingulate Cortex Activation by Emotional Words: fMRI Evidence From a Valence Decision Task, Human Brain Mapping, 2003, p. 30-41, 18, Wiley-Liss, Inc.

Nichols, Thomas E. and Homes, Andrew P., Nonparametric Permutation Tests for Fuhctional Neuroimaging: A Primer with Examples, Human Brain Mapping, 2001, p. 1-25, 15, Wiley-Liss, Inc.

Ofek, E., and Pratt, H., Neurophysiological correlates of subjective significance, Clinical Neurophysiology, 2005, p. 2354-2362, 116, Elsevier Ireland Ltd.

Ofek, E., and Pratt, H., A questionnaire for quantifying subjective significance of names: Physiological validation with PAT, Physiology & Behavior, 2008, p. 368-373, 94, Elsevier Inc.

Pascual-Marqui, R.D., et al., Low resolution electromagnetic tomography: a new method for localizing electrical activity in the brain, International Journal of Psychophysiology, 1994, p. 49-65, 18, Elsevier Science B.V.

Pascual-Marqui, R.D., Review of Methods for Solving the EEG Inverse Problem, International Journal of Bioelectromagnetism, 1999, p. 75-86, vol. 1, No. 1.

Pascual-Marqui, R.D., et al., Functional imaging with low resolution brain electromagnetic tomography (LORETA): review, new comparisons, and new validation, Japanese Journal of Clinical Neurophysiology, 2002, p. 81-94, 30.

Perrin, Fabien, et al., A differential brain response to the subject's own name persists during sleep, Clinical Neurophysiology, 1999, p. 2153-2164, 110, Elsevier Science Ireland Ltd.

Shekhar, Anantha, et al., The Amygdala, Panic Disorder, and Cardiovascular Responses, Annals New York Academy of Sciences, 2003, p. 308-325, 985.

* cited by examiner

SUBJECTIVE SIGNIFICANCE EVALUATION TOOL, BRAIN ACTIVITY BASED

FIELD OF THE INVENTION

The present invention relates to a method and system for determining the subjective state of mind of a human subject and in particular to assessment of neurophysiologic manifestations of subjective significance.

BACKGROUND OF THE INVENTION

The neural substrates of emotional response have traditionally been studied using universal sets of emotionally loaded stimuli, regardless of their subjective significance to the individual subject. Assessment of the unique brain response to subjectively significant stimuli has not been studied before.

Deception is probably the best-studied mind states of all; most of the present lie-detection testing techniques use polygraph devices to examine the peripheral autonomic response to relevant versus irrelevant questions. Present day polygraph devices can combine measurements of electrodermal skin conductance, blood pressure, respiration and peripheral vasomotor activity, minute changes in vocal response and face temperature. The increase in autonomic response is interpreted as an attempt to deceive by the investigated subject. This basic principle behind polygraph machine hasn't changed since its invention over 80 years ago.

Lately, a newer method for lie detection which is based on examining the amplitude of the P300 component of event-related brain potentials was proposed (Farwell, L. A. & Smith, S. S. J. Forensic Sci. 46, 135-143, 2001). When a human subject is exposed to something that already is stored in memory, the brain emits an electrical response called a P300 wave. The P300 is a non-specific brain response, elicited in response to innovation, subject's own name, surprise and task related stimuli. This phenomenon occurs approximately 300 milliseconds after a meaningful stimulus. The investigators extrapolate from an Electro-Encephalo-Graphy (EEG) recording clues to differentiate between relevant and irrelevant stimuli.

Another important known technique for mind state detection is the functional magnetic resonance imaging (fMRI). Images of the brain can be taken during activity at rest and during a specific behavior, thus demonstrating the function of a particular area of the subject's brain as well as its structure. An extensive research is performed to detect the part of the brain active during a lie. There are a number of reports in the literature about success in detecting deception (Langleben, D. D. et al. Neurolmage 15, 727-732, 2002), (Kozel F. A. et al. Behav Neurosci. 2004 August; 118(4): 852-6), (Ganis G et al. Cereb Cortex. 2003 August; 13(8): 830-6), a number of brain regions were found to participate in the deceptive response. This is an important discovery, since even though a subject might control his autonomic responses, the very thought of deception will be detected. A few studies were also done concerning the subjective emotional experience of subjects. However, fMRI require a large and expensive and non-mobile instrumentation, and cannot get results within milliseconds resolution.

SUMMARY OF THE INVENTION

It is an object of the present invention to define brain activity to subjectively significant stimuli.

Another object of the present invention is to characterize the time course of activity in the brain areas involved when exposed to subjectively significant stimuli.

It is yet another object of the present invention to decide if a given stimulus is subjectively significant or not to a human subject.

The present invention thus relates to a method for determining the subjective state of mind of a human subject presented with a test stimulus and to a system for implementing said method. The method comprises the following steps:

(i) connecting an electroencephalogram (EEG) recording unit to the human subject;
(ii) presenting human subject with one or more test stimuli;
(iii) recording the human subject's EEG;
(iv) performing a 3-D reconstruction of the recorded EEG signal in order to visualize the brain areas that were active when presenting the test stimuli; and
(v) comparing human subject's reactions to test stimuli to reference data in order to determine if said one or more test stimuli are subjectively significant or not.

The invention aims to determine if a given stimulus is subjectively meaningful to an individual or if it is neutral to that individual.

Preferably, several repetitions of the stimuli are used, so that event related potentials (ERP) are recorded to enhance the signal to noise ratio. The test stimuli are compared with reference data that can be obtained from two sources: reactions to reference stimuli and/or predetermined mapping of certain brain area known to be activated during different mind states.

In addition, the EEG signal is also recorded shortly before the stimulus is given in order to identify how the brain is active before being exposed to the stimulus.

Measuring the reference stimuli is done in a similar way to measuring the reactions to test stimuli. The human subject is presented with two sets of stimuli: a first set that comprises neutral, that is non-subjectively significant stimuli for that individual; and a second set that comprises subjectively significant stimuli for that individual. Measuring the reference stimuli is obtained using the following steps: (i) connecting an electroencephalogram (EEG) recording unit to the human subject; (ii) preparing a list of significant and non significant reference stimuli; (iii) providing reference stimuli to the subject and recording his ERP; (iv) using a computer unit to receive the recorded EEG and perform 3-D reconstruction of the EEG signal; and (v) performing analysis of subject mental reaction to reference stimuli.

The test stimuli 3-D reconstruction is compared to the 3-D reconstruction of neutral and subjectively significant stimuli in order to assess if the test stimuli are subjectively significant or not.

The test stimuli, as well as the reference stimuli, can be provided through common audio-visual means such as earphones, a computer screen, a television monitor etc. The stimulus is controlled by a computer unit so that the time of delivering the stimulus is controlled with great precision. The EEG measures the responses in different brain areas mostly between 200 milliseconds (ms) and 950 ms after a stimulus is delivered.

Optionally, Peripheral arterial tonometry (PAT) recordings can be used to check peripheral autonomic response. PAT can be used instead of EEG readings, though the results are less precise.

One or more human subjects are presented with a set of subjective significant stimuli and a set on neutral stimuli. The EEG signals recorded are transformed to 3D maps of different brain parts active at a given time point after the stimulus is received. The end result is two set of maps of activities of different brain parts at a given time point after the stimulus is received. One set of maps corresponds to a neutral stimulus and the other set of maps corresponds to a subjectively significant stimulus. Then if we wish to determine if a new stimulus is subjectively significant or not to a given individual, we can measure the brain activity after receiving the stimulus and compare the reconstructed brain maps with the previous two sets of maps for neutral or subjectively significant stimuli. Comparing the new map to the two reference maps (neutral and subjectively significant stimuli) will allow us to determine if the new stimulus is subjectively significant or not according to the resemblance of the new brains maps with either the brain maps for neutral stimuli or the brain maps for subjectively significant stimuli.

The invention may be used in a variety of applications including but not limited to: a psychological evaluation tool, a tool for identification of subjectively significant response in comatose patients, a tool for identification of a specific response in demented patients, a tool for evaluation of psychological response in psychiatric patients and autistic children, a tool for evaluation of subjectively significant response in locked in syndrome patients, and as a lie detector.

Subjective significance evaluation tool, brain activity based, may also serve as a tool for evaluating residual specific brain activity in patients with no motor response, as in comatose patients, locked in syndrome, or demented patients. It may also serve the evaluation of specific response in clinically depressed patients, or autistic children. In many psychiatric disorders, the therapy is difficult to achieve since the patient is not cooperative, and in many cases is not even aware of the subconscious conflicts and drives which cause his/hers illness.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
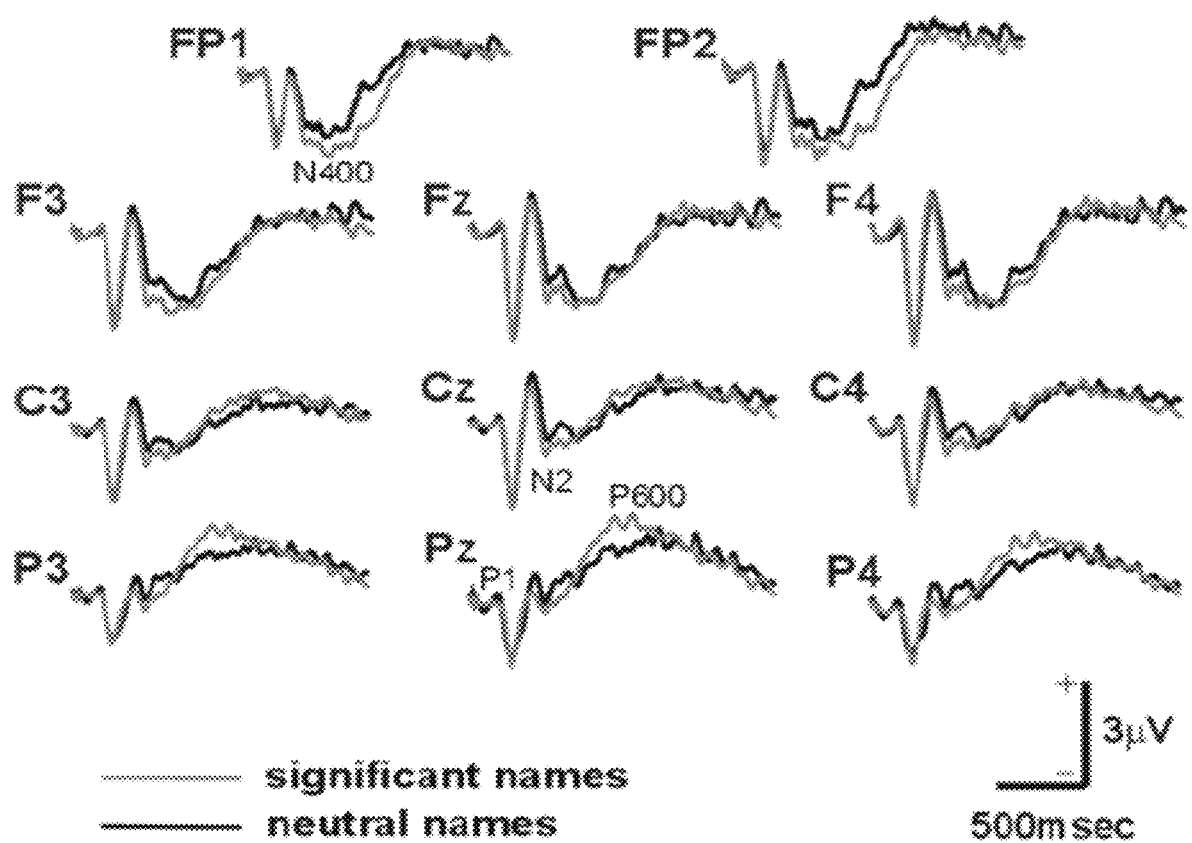
FIG. 1 shows event related potentials (ERP) to subjectively significant and neutral names, grand average across 16 subjects, from 11 electrodes: Fp1, Fp2, F3, Fz, F4, C3, Cz, C4, P3, Pz, P4. Main ERP components are marked: P 1, N2, N400, P600. Note the enhanced components N2, N400 and P600 to subjectively significant stimuli.

In the following detailed description of various embodiments, reference is made to the accompanying drawings that form a part thereof, and in which are shown by way of illustration specific embodiments in which the invention may be practiced. It is understood that other embodiments may be utilized and structural changes may be made without departing from the scope of the present invention.

Human behavior is affected by the subjective significance of events. The present invention aims to define brain activity to subjectively significant stimuli, and characterize the time course of activity in the brain areas involved. Previous studies on the neural basis of emotions were typically fMRI or PET studies (Crosson et al., 2002; Elliott et al., 2000, 2002; George et al., 1995; Gundel et al., 2003; Maddock et al., 2003) whose temporal resolution is in the order of seconds, whereas neural activity related to emotional processing and behavior is in the sub-second range. The present invention records Event-Related Potentials (ERPs) from the scalp and uses current density source estimation (Low-Resolution Electromagnetic Tomographic Analysis—LORETA; Pascual-Marqui et al., 1994; Pascual-Marqui, 1999; Pascual-Marqui R D, Michel C M, Lehmann D. Low resolution electromagnetic tomography: a new method for localizing electrical activity in the brain. International Journal of Psychophysiology 1994, 18:49-65) to trace brain activity with temporal resolution of milliseconds and spatial resolution in the order of millimeters.

The neurophysiological basis of emotional response to stimuli has, for the most part, been studied assuming the same affective valence for each stimulus across all subjects (Bremner et al., 2001; Dietrich et al., 2001; Elliott et al., 2002; Hamann and Mao, 2002). Previous studies have demonstrated the involvement of a neural network consisting of the prefrontal cortex, both temporal lobes and cingulate gyrus, in addition to other subcortical areas (amygdala, hippocampus), in the emotional response to stimuli (Crosson et al., 2002; Devinsky et al., 1995; Elliott et al., 2000; Elliott et al., 2002; Esslen et al., 2004; George et al., 1995; Imaizumi et al., 1997; Maddock and Buonocore, 1997; Maddock et al., 2003). Contradictory results were reported by studies that used such uniform sets of stimuli, regarding the involvement of certain areas (e.g. anterior cingulate gyrus, see Blair et al., 1999, and Esslen et al., 2004) and also regarding hemispheric lateralization of the emotional response to stimuli (Jones and Fox, 1992; Davidson and Irwin, 1999; Esslen et al., 2004).

The invention uses subjective significance to the individual subject, rather than universal (objective) affective valence which is assumed to be the same across all subjects. In general, subjectively significant stimuli are more prone to evoke behavior than other stimuli. When the same set of stimuli, assumed to be universally affective, is used for all subjects, individual stimuli may have different affective valence for different subjects. Thus, comparing brain activity to such stimuli across subjects, for whom the same stimulus may carry a different subjective significance, does not allow isolating the net effect of affective valence.

For example, most verbal stimuli have more than one meaning and may have several connotations; which complicates the determination of their subjective affective valence. In contrast, the subjective significance of first names is mostly acquired from people familiar to the subject that carry the name. Therefore, first names may be suitable for studying the neurophysiological correlates of emotional significance. Furthermore, the very same first name may have an emotional value to some subjects and be neutral to others, providing a better control for the net effect of subjective emotional significance of the very same stimulus, than comparing different words. Several studies have demonstrated the neural response to the subject's own name compared to neutral names (Berlad and Pratt, 1995; Perrin et al., 1999; Kampe et al., 2003). A comparison of the neural response to any subjectively significant names with that to neutral names has not been reported. Moreover, previous studies describing the neural response to the subject's own name did not trace the exact time course and order of activation of the brain areas involved.

The present invention identifies the specific neural response to subjectively significant stimuli and traces neural correlates of subjective emotional response. The general brain response evoked by all subjectively significant stimuli, with both negative and positive valence is captured. Moreover, because some subjectively significant stimuli may have a mixed negative and positive connotation (e.g. the subject's mother, depending on the context and personal experience), brain responses to subjectively significant stimuli are more readily defined than to stimuli classified as 'positive' or 'negative'.

Results of experiments conducted show a consistent and uniform pattern of brain response to subjectively significant stimuli across all subjects of the same group. In each of the subjects the response to subjectively significant stimuli included neural activity in earlier time frames and in additional brain areas compared to the response to neutral stimuli. Activation up to 200 ms from stimulus onset was apparently not uniform enough across subjects to be statistically significant. During this early time period, several brain areas may have been differentially involved but did not attain significance in our analysis because of different time courses of activation to different stimuli in different subjects. The general features that were statistically significant across all subjects show that brain response specific to subjectively significant stimuli is characterized by 3 features: (1) generalized enhancement of cortical activity; (2) a specific localized response involving several distinct and concurrently active brain areas at different times; (3) late (>700 ms) activity unique to subjectively significant stimuli, after the activity to neutral stimuli has subsided. The generalized enhancement of activation (see statistical results and FIGS. 2 and 3) may be part of an arousal response mediated by the amygdala and other parts of the limbic system (Critchley, 2003; Jones, 2003; Shekhar et al., 2003). Significant amygdalar activation was not found in our study, most probably because of its deep location within the brain and the fact that its neurons are not spatially aligned.

According to one embodiment of the present invention, any audio and/or visual stimulus can be tested if it is subjectively significant to an individual, by creating 3-D reference maps of neutral and subjectively significant stimuli delivered to other individuals from the same group. Defining the group of similar individuals depends on the context of what is needed to be tested. If the stimulus tested is a word in a given language, as in the experiment described below, than all the individuals need to be speakers of the same language. If the stimulus to be tested is a visual stimulus of a technical object, the group of reference individuals needs to be familiar with the technical object in order to test if it is subjectively significant. Other factors may also be determined in order to create a homogenous reference group, for example, age, health, right-handed or left handed people, sex, education etc.

According to another embodiment of the present invention, reference stimuli can be measured in a group of reference individuals that is not homogeneous.

When measuring reference stimuli, subjectively significant stimuli can be determined by various non-exclusive methods, for example, a questionnaire, an interview or prior knowledge about the individual or subject.

The present invention can be used in a variety of applications, for example:

1. Truth detection:

The present invention can serve as an important tool for legal investigations, including screening of court witnesses for intention to lie or a tool to probe the mental response of the prosecuted individual to crime evidences. Another use of the invention is in job screening and in other fields the polygraph device is currently used. Another application is in crime investigation whereas one can present suspects with a number of probes that are unique details of a crime that only the culprit could know. A guilty subject is expected to have memory of these probes and therefore treat them differently than the innocent person.

2. Brain computer interface (BCI):

Current methods for using mental information to activate computers or robots are based on plain EEG signals or on invasive devices. Although individuals can learn to control and change at will certain aspects of the EEG signal, the current rate of information transfer with plain EEG recording is very low. In one embodiment, the present invention enables to perform online 3D reconstruction of the signal to capture the full potential of the data encoded in the EEG.

3. Improvement of psychotherapeutical treatment.

The psychiatric staff meets many problems diagnosing and treating these subjects, since the behavior response is not a good indication concerning the success/failure of the therapy. The present invention can serve in psychological and psychiatric investigation, in order to find what is really important to the patient, or what is the source of the problem, in order to build a therapeutic plan and find out what should be the focus of the therapy. A mental response reader which is able to reveal specific response to therapeutic inquiries can greatly assist in the treatment of a range of mental conditions such as autistic, psychotic and depressed patients and patients with post traumatic stress disorder (PTSD). In addition, especially in PTSD patients the present invention enables identifying stimuli which are related to the trauma, which will be efficient to expose the patient to, or to avoid.

4. In 'locked in' and comatose patients, in whom the level of cortical activity can be probed and specific brain activity to significant stimuli will be assessed (the technique of the invention also allows for quick testing whether the comatose patient is able to hear or to see).

5. Revealing information (and subjective significance of objects) in patients who are unable to talk—in autism, locked in syndrome, comatose patients, severely disabled patients or patients in a catatonic condition; and in patients who are unwilling to talk (a lie detector).

Experiment Conducted

1. Methods 1.1 Subjects

Sixteen right handed, native Hebrew speaking, healthy normal volunteers (7 males and 9 females; mean age: 22.7, SDZ2.8 years) with no hearing complaints nor evidence of neurological disorders participated in this study. Since subjects' first names were used as auditory stimuli in the experiment, subjects were chosen so that their first names were 2 syllable common Hebrew names, which began with a sonorant. Subjects were paid for their participation. Experimental procedures were approved by the Institutional Review Board for experiments involving human subjects (Helsinki Committee). 1.2 Experimental Procedure Potentials were recorded from tin electrodes placed according to the 10-20 system in an electrode cap (Electro-Cap International Inc., Eaton, Ohio, USA). Activity was recorded (Ceegraph IV Biologic Systems Corp. IL, USA) from 19 locations: Fp1, Fp2, F7, F3, Fz, F4, F8, T3, C3, Cz, C4, T4, T5, P3, Pz, P4, T6, O1, O2. Three additional tin electrodes, external to the cap, were attached to the right and the left mastoids (A1 and A2), and a third below the left eye, referenced to Fz, to monitor eye movements (EOG). In total, EEG was recorded from a 21-electrode array, in addition to an EOG channel. A ground electrode was placed on the left forearm. All EEG electrodes were referenced to an electrode midline on the chin, far from the brain, from facial and lingual muscles and in the midline, thus avoiding asymmetry distortions. Impedance at each electrode was maintained below 5 kΩ.

Subjects listened to names presented binaurally by earphones and performed an identification task, pressing a button in response to each of 3 target names ending with a pre-assigned consonant, from a repertoire of 29 names. Subjects performed the task reclining in an adjustable armchair in an acoustically isolated chamber. Subjects were instructed to avoid eye movements and blinking as much as possible, and to keep their gaze on a fixed point in front of them during task performance.

1.3 Stimuli

All stimuli were two syllable (700 ms duration) common Hebrew first names, beginning with a sonorant so that all stimuli had similar acoustic onset properties. In each experiment, 29 names were randomly repeated. The stimuli were identical for each group of 4 subjects, and included the subjects' own names, and 5 names of important persons in each subject's life (a present or former spouse, close family members, close friends, and a hated person). Any given name in the list was thus subjectively significant to at least one member of the group and was neutral to others. The stimuli also included 3 target names that ended with the same consonant. Target names were neutral to all subjects. Data about names of important persons in the subject's life were collected during a short interview 1-2 months before the experiment. Final assessment of the subjective significance and affective valence of each of the names in the list was conducted by an interview after the experiment.

Stimuli were recorded from a native Hebrew speaker and saved as digitized sound files. Stimuli were presented binaurally with an inter-stimulus interval (between the onset of a name and onset of the following name) of 2.2 s.

1.4 Experimental Paradigm

Subjects were instructed to press a button when they heard a name that ends with a certain consonant (target name). Subjects received 10 blocks, each consisting of 7 randomly distributed repetitions of each of the 29 names in the list. The list of names included in the experiment was identical for each group of 4 subjects. Short breaks were taken after each block.

1.5 Interview

Subjective affective significance of each name was assessed after the experiment in an interview, based on a structured questionnaire which was validated both statistically and by using an autonomic activity measure (peripheral arterial tonometry). The subject was asked about each name separately. The questionnaire included 46 dichotomous and rating questions for each person bearing each name. A subjective significance score was computed accordingly for each name, for each subject. Names with scores higher than a standard deviation above the subject's own score averaged across all names were considered subjectively significant to that subject, and names with scores lower than a standard deviation below the subject's own averaged score were considered neutral.

For each subject, names were ranked according to their individual affective significance. Thus, a given name could be significant to one subject and neutral to another, and the net effect of subjective significance on brain activity could be isolated.

1.6 ERP Recording and Measurement

Potentials from the EEG (×100,000) and EOG (×20,000) channels were amplified, filtered (0.1-100 Hz, 6 dB/octave slopes), digitized with a 12 bit A/D converter at a rate of 256 samples/s, and stored for subsequent off-line analysis.

Continuous records were segmented beginning 300 ms pre-stimulus until 2700 ms after stimulus onset (3 s total analysis time), and averaged after eye-movement correction based on eye-channel/EEG correlations (Attias et al., 1993).

Potentials were averaged separately for each non-target first name, for each subject. Potentials to target names were not included in the analysis. Thus, all the stimuli whose responses were analyzed, neutral and subjectively significant, were non-targets in this task. Two separate averages were derived for each subject: (1) for the 3 most subjectively significant names; (2) for the 3 least subjectively significant ('most neutral') names, according to the interview results (see above). In this report, ERPs to all subjectively significant names were averaged together, irrespective of positive or negative valence. The effects of valence will be reported in a separate report. The averaged ERPs were low-pass filtered with a cutoff at 20 Hz.

1.7 Current Density Estimations and Statistical Analysis

Neural sources of scalp-recorded potentials were estimated using the LORETA procedures for estimating source current density distribution in a 3D Talairach space of the brain's gray matter. The LORETA procedure computes current density under the assumption that for each voxel the current density should be as close as possible to the average current density of the neighboring voxels ('smoothness assumption'). LORETA has been shown to have a 7 mm spatial resolution, and found superior to other localization methods in localizing deep (subcortical) sources (Pascual-Marqui et al., 1994; Pascual-Marqui, 1999; Pascual-Marqui et al., 2002).

LORETA current density estimations were performed on each subject's ERP waveforms, separately for subjectively significant and for neutral names. In order to negate non-specific effects related to readiness and motor preparation, a baseline level and distribution of activity was defined as the average for each voxel over the 100 ms preceding stimulus onset. Only activity significantly different than this baseline activity was analyzed. Significance of activity was determined by nonparametric (SnPM) paired comparisons of time frame by time frame current density in each voxel with baseline, in the 800 ms following name onset. The SnPM method estimates the probability distribution by using a randomization procedure; it corrects for multiple comparisons, and has the highest possible statistical power (Nichols and Holmes, 2002). Specifically, in our study we used the 'pseudo-t' statistic which reduced noise in the data by averaging over adjacent voxels (Nichols and Holmes, 2002). Comparisons were conducted separately for subjectively significant and for neutral names, compared to baseline. An additional comparison (SnPM) was conducted for the responses to subjectively significant compared to neutral names. Level of activation in each area was computed as the percentage of voxels in the vicinity of a specific area that were significantly active at a given time frame, multiplied by their average t value. Analysis of Variance procedures were conducted in order to assess the effects of subjective significance (significant vs. neutral), laterality (left vs. right hemisphere) and their interaction on brain activity. Probabilities below 0.05, after Geisser-Greenhaus and Bonferroni corrections (when appropriate), were considered significant.

2. Results

FIG. 1 presents the potentials recorded from 11 of the 21 channels, in response to subjectively significant and to neutral names. Overall, subjectively significant stimuli were associated with enhanced activity relative to neutral stimuli. Table 1 summarizes activity in the vicinity of areas found to be significantly active above baseline ($P<0.05$) in response to subjectively significant and to neutral names during different time periods after stimulus onset. The main areas specifically involved in response to subjectively significant stimuli were in the vicinities of Wernicke's area and Wernicke's homologous area in the right hemisphere, of Broca's area, of left middle, medial and superior frontal gyri (at different times), of the right auditory cortex, of the left hippocampus and of the left precuneus.

TABLE 1

Areas involved in the response to subjectively significant and neutral stimuli

| Latency (ms) | Areas involved in response to both neutral and subjectively significant stimuli | | Areas involved only in response to subjectively significant stimuli | |
|---|---|---|---|---|
| | Left hemisphere | Right hemisphere | Left hemisphere | Right hemisphere |
| 200-350 | Central cingulate G. | Mid. temporal G. Sup. temporal G. Insula | | Wernicke's homologue area |
| 350-500 | Ant. cingulate G. Central cingulate G. Inf. Frontal G. Med. frontal G. Rectal G. Subcallosal G. Inf. parietal lobule Wernicke's area Broca's area Insula Sup. temporal G. Precentral G. Ant. cingulate G. | Ant. cingulate G. Central cingulate G. Inf. frontal G. Med. frontal G. Rectal G. Sup. temporal G. Insula Precentral G. Parahippocampal G. Subcallosal G. Uncus | Sup. frontal G. Mid. frontal G. Supramarginal G. Postcentral G. | Orbital G. Mid. temporal G. Inf. temporal G. Wernicke's homologue area |
| 500-600 | Ant. cingulate G. Central cingulate G. Med. frontal G. Mid. frontal G. Sup. frontal G. Rectal G. Subcallosal G. Parahippocampal G. Hippocampus Insula Sup. temporal G. Uncus Precentral G. | Ant. cingulate G. Central cingulate G. Inf. frontal G. Med. frontal G. Sup. frontal G. Rectal G. Subcallosal G. Uncus Parahippocampal G. | Wernicke's area Broca's area | Mid. temporal G. Sup. temporal G. |
| 600-700 | Ant. cingulate G. Central cingulate G.. Med. frontal G. Inf. Frontal G. Sup. Frontal G. | Ant. cingulate G Central cingulate G. Inf. frontal G. Med. frontal G. Mid. frontal G. Sup. frontal G. | Wernicke's area Broca's area Mid. frontal G. Precentral G. Sup. temporal G. Inf. temporal G. | Insula Precuneus |

TABLE 1-continued

Areas involved in the response to subjectively significant and neutral stimuli

| Latency (ms) | Areas involved in response to both neutral and subjectively significant stimuli | | Areas involved only in response to subjectively significant stimuli | |
| --- | --- | --- | --- | --- |
| | Left hemisphere | Right hemisphere | Left hemisphere | Right hemisphere |
| | Insula | Rectal G. | Inf. parietal lobule | |
| | | | Sup. paritetal lobule | |
| | | | Precuneus | |
| | | | Postcentral G. | |
| | | | Hippocampus | |
| 700-800 | Ant. cingulate G. | Ant. cingulate G. | Broca's area | Sup. frontal G. |
| | Central cingulate G. | Central cingulate G. | Mid. frontal G. | Mid. frontal G. |
| | Sup. frontal G. | Inf. frontal G. | Inf. frontal G. | |
| | Med. frontal G. | Med. frontal G. | Precentral G. | |
| | Rectal G. | Rectal G. | Sup. temporal G. | |
| | Precuneus | Orbital G. | Insula | |

Abbreviations used:
G, gyrus;
Ant., anterior;
Mid, middle;
Sup, superior;
Inf, inferior;
Med, medial.

Figure 2:
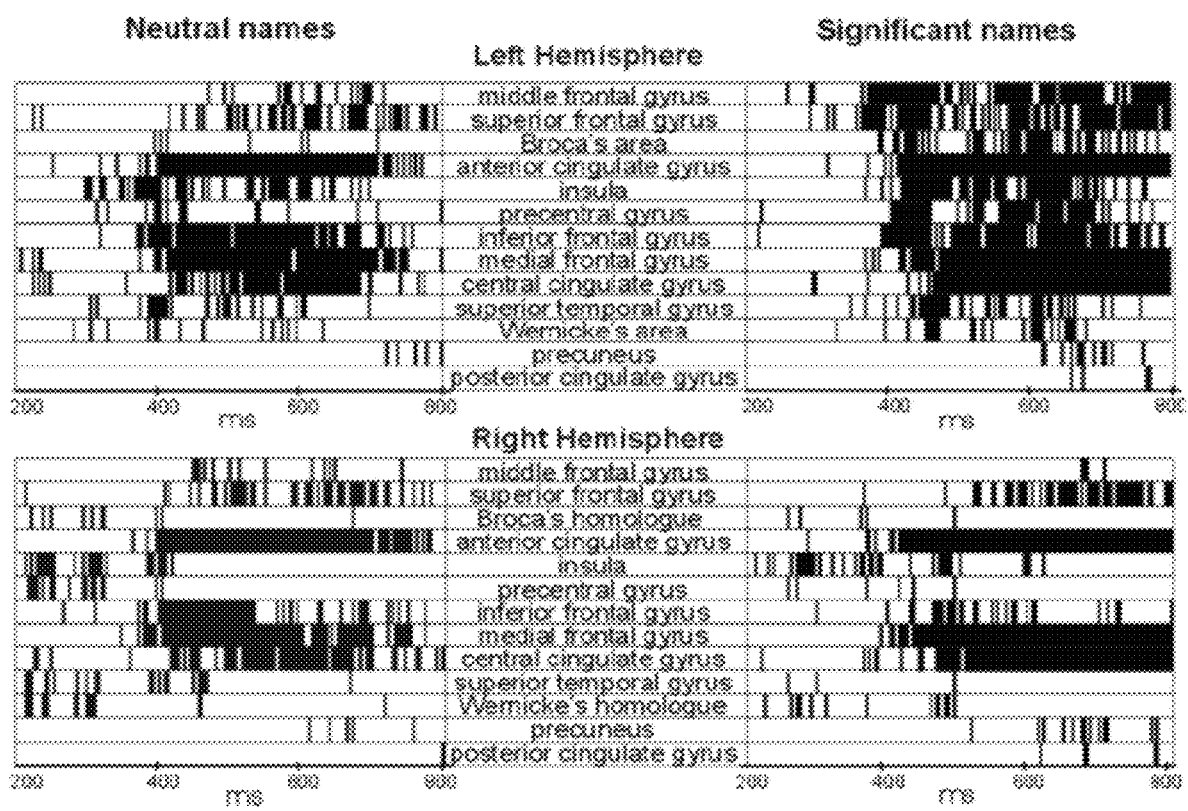
FIG. 2 illustrates the time course of statistically significant activation in the vicinity of 13 areas in each hemisphere to subjectively significant and neutral names, indicated by time frames marked in black. Note that responses to subjectively significant stimuli are: (1) overall enhanced compared to neutral names, more so in the left—compared to the right hemisphere; (2) particularly enhanced in the vicinities of the middle and superior frontal gyri, Broca's area, Wernicke's area, insula, precentral gyrus, precuneus and posterior cingulate gyrus in the left hemisphere; (3) prominent in the later time frames in the vicinity of the middle, superior, and medial frontal gyri, as well as in the vicinity of the anterior, central and posterior cingulate gyri.
Figure 3A:
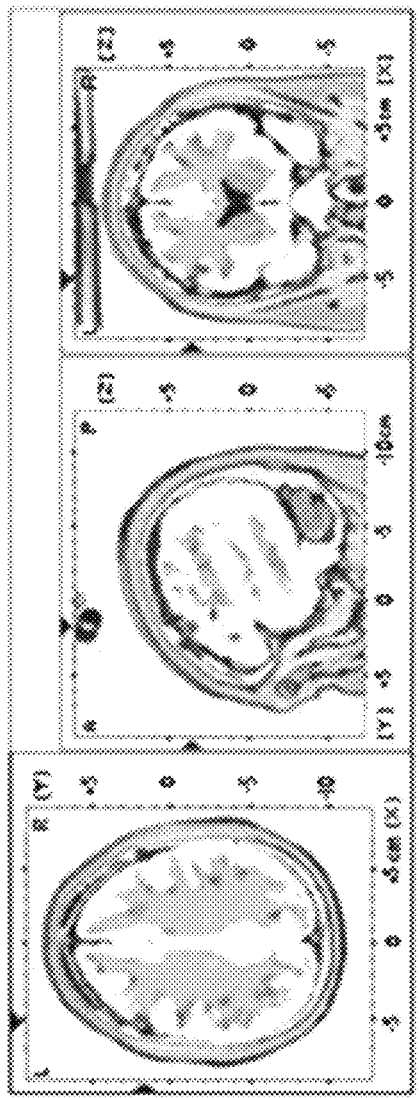
FIG. 3 illustrates the time course and level of significant activation in the vicinity of specific brain areas in response to subjectively significant vs. neutral stimuli. Level of activation in the vicinity of each area was computed as the percentage of voxels in the area that were significantly active at a given time frame, multiplied by their average t value. The sections in the middle column of the figure show activation in the vicinity of a given area in response to subjectively significant stimuli, at the time of its peak activation, marked by an arrow on the graph. The respective time courses of activation in the vicinity of each area, from 200 to 800 ms after stimulus onset, in response to subjectively significant and to neutral stimuli, are also shown. Note: (1) Enhanced activation in response to subjectively significant stimuli; (2) differential pattern of activation in the vicinity of concurrently active areas in response to subjectively significant compared to neutral names; (3) prominence of the response in left hemisphere; (4) earlier onset of activation in the vicinity of the left middle frontal gyrus in response to subjectively significant stimuli.
Figure 3A:
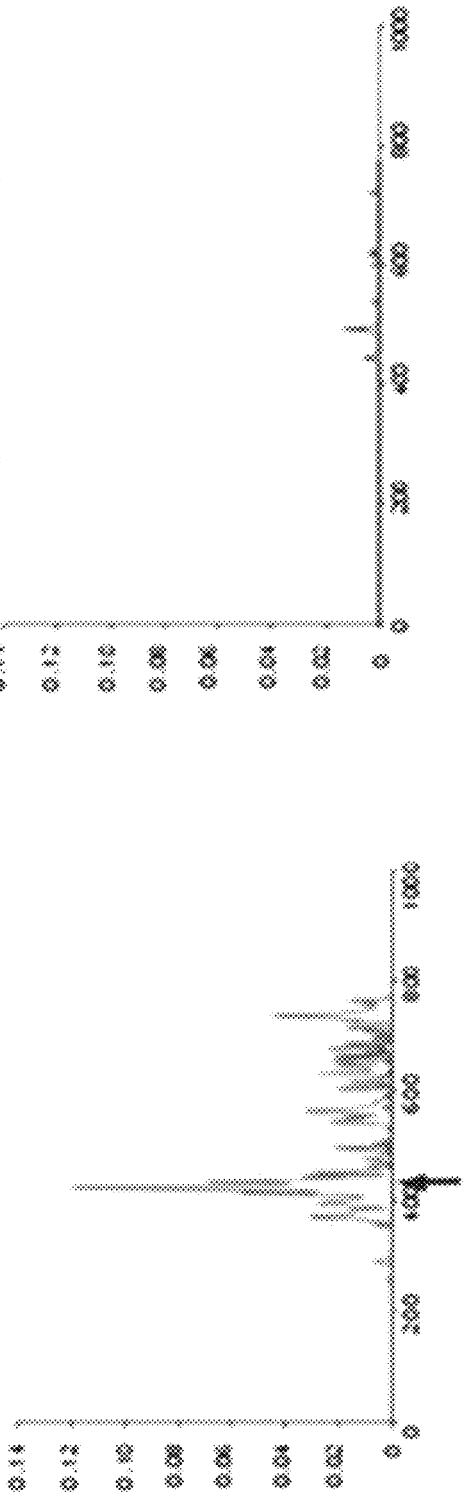
Figure 3B:
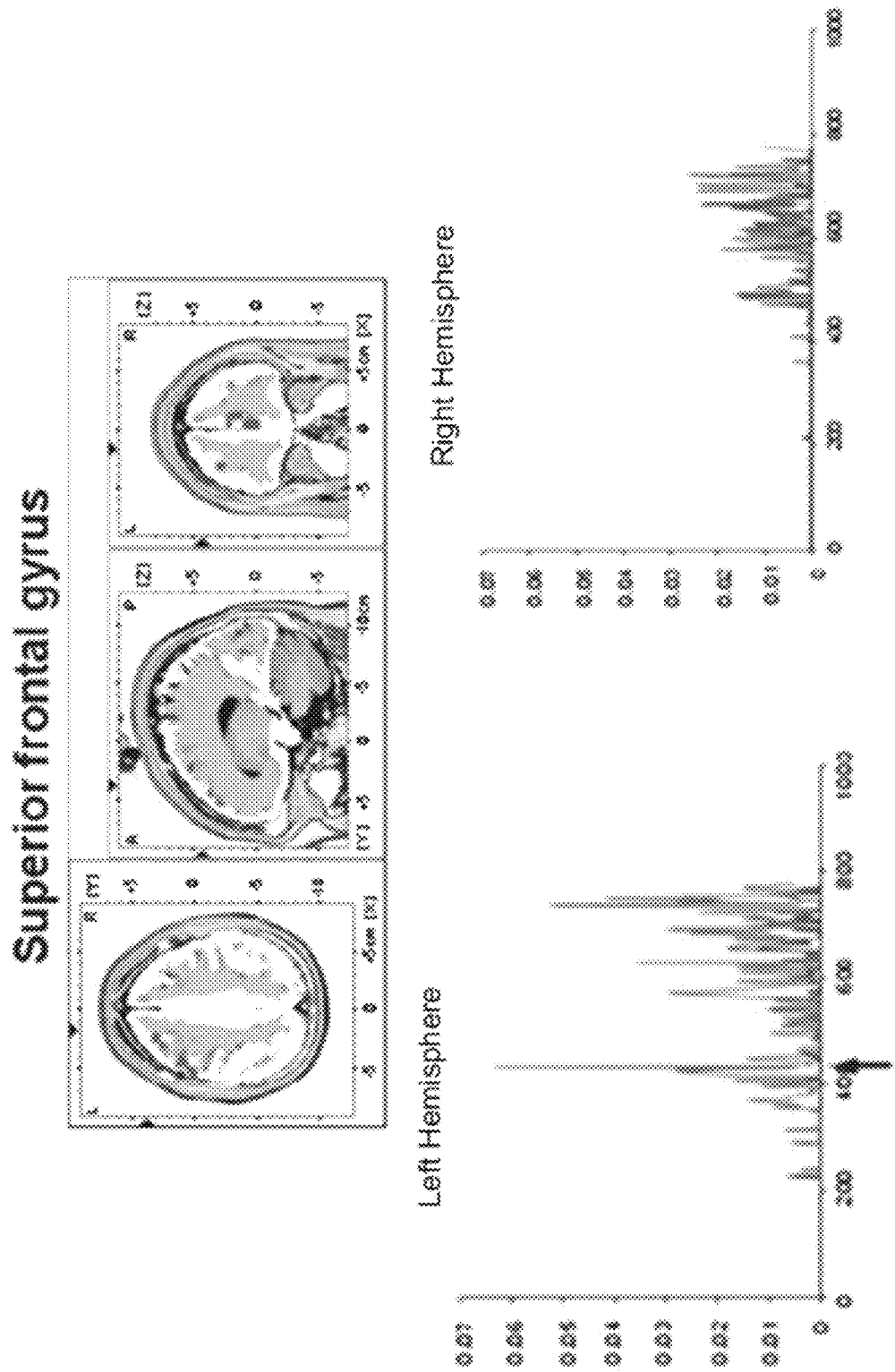
Figure 3C:
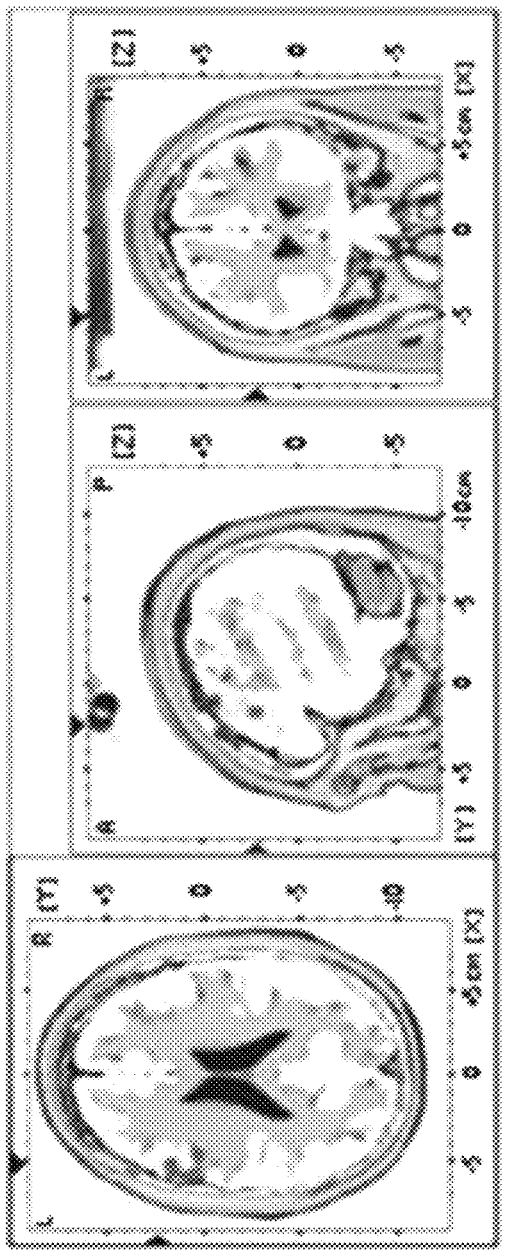
Figure 3C:
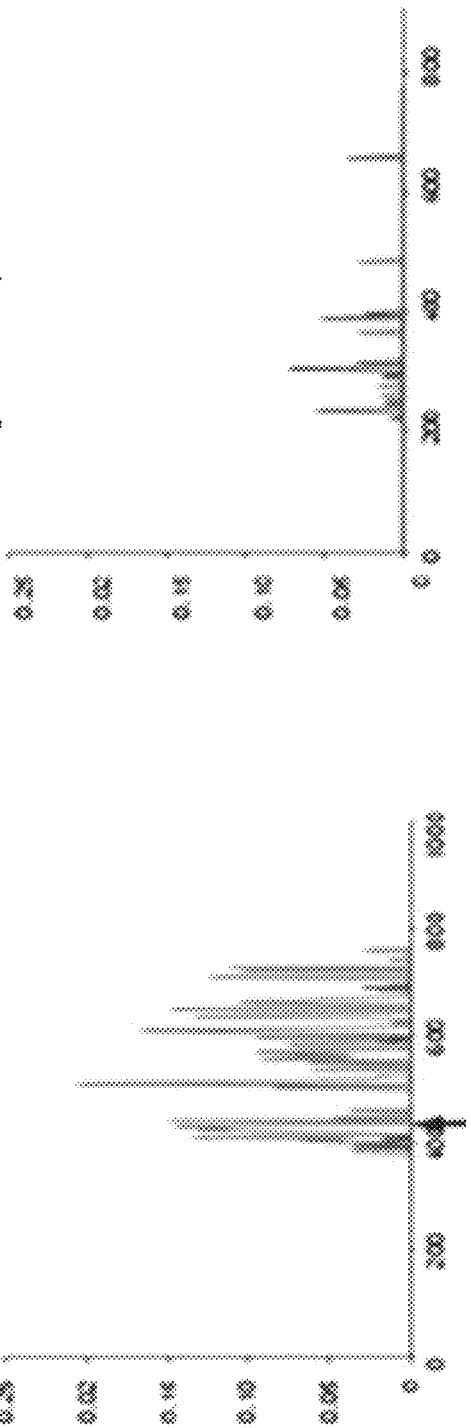
Figure 3D:
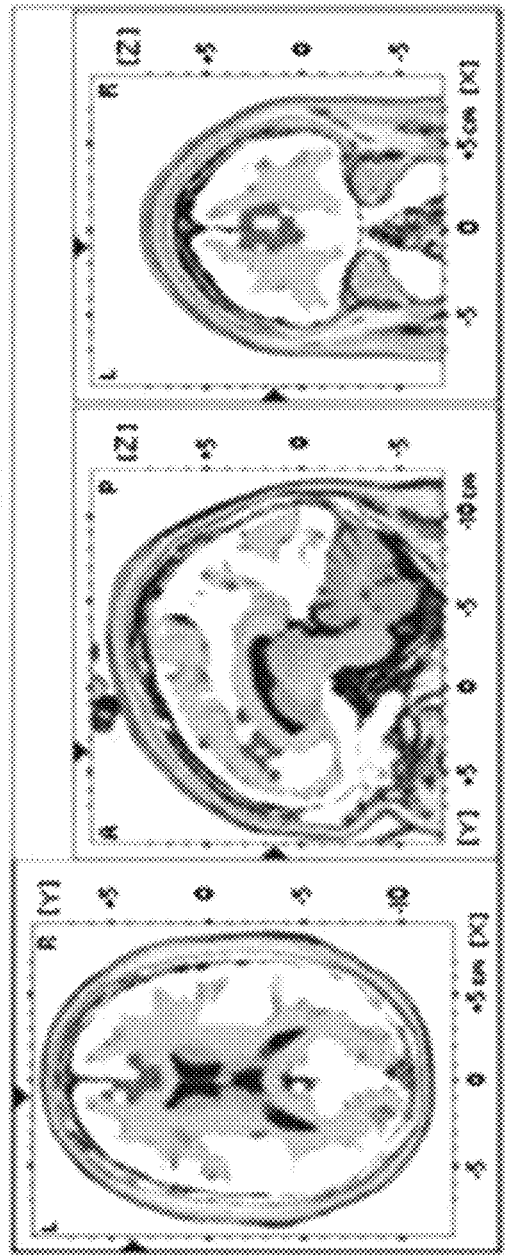
Figure 3D:
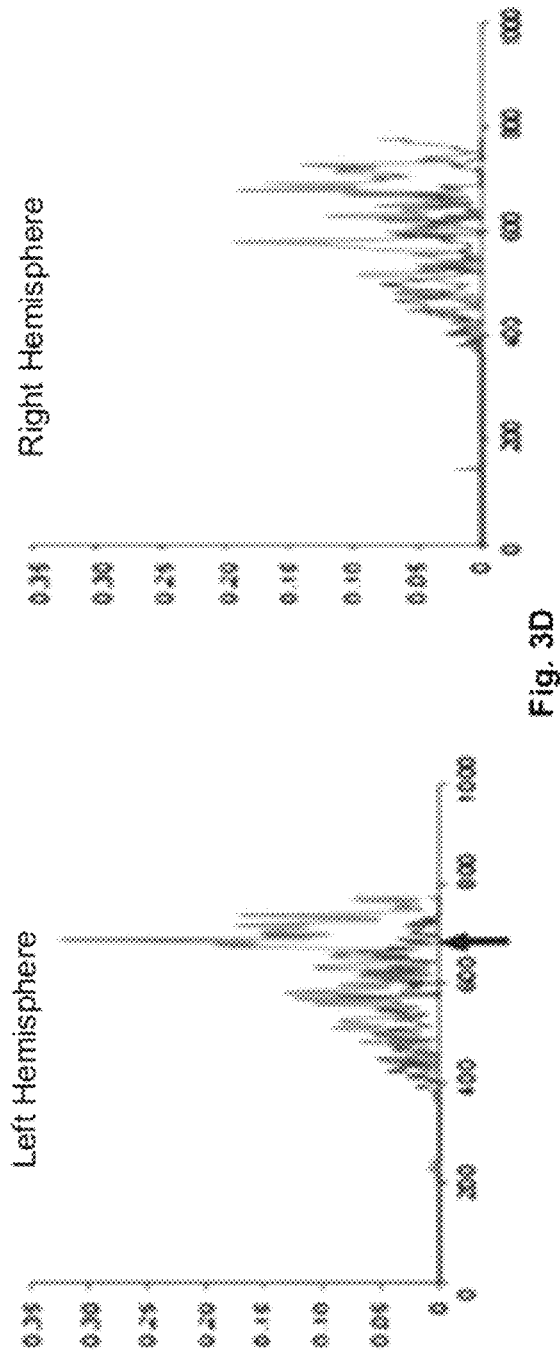
Figure 3E:
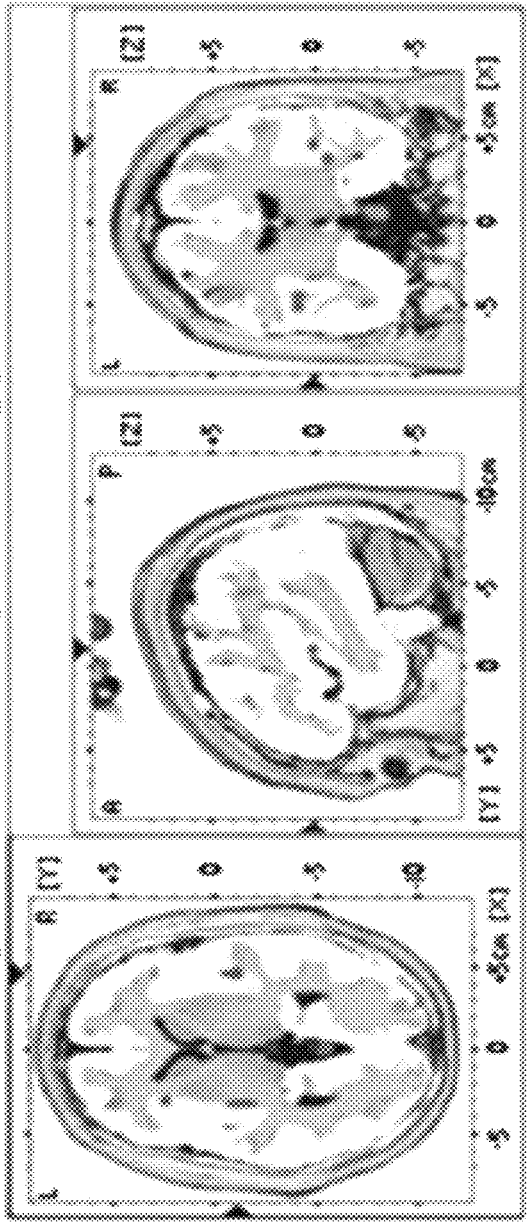
Figure 3E:
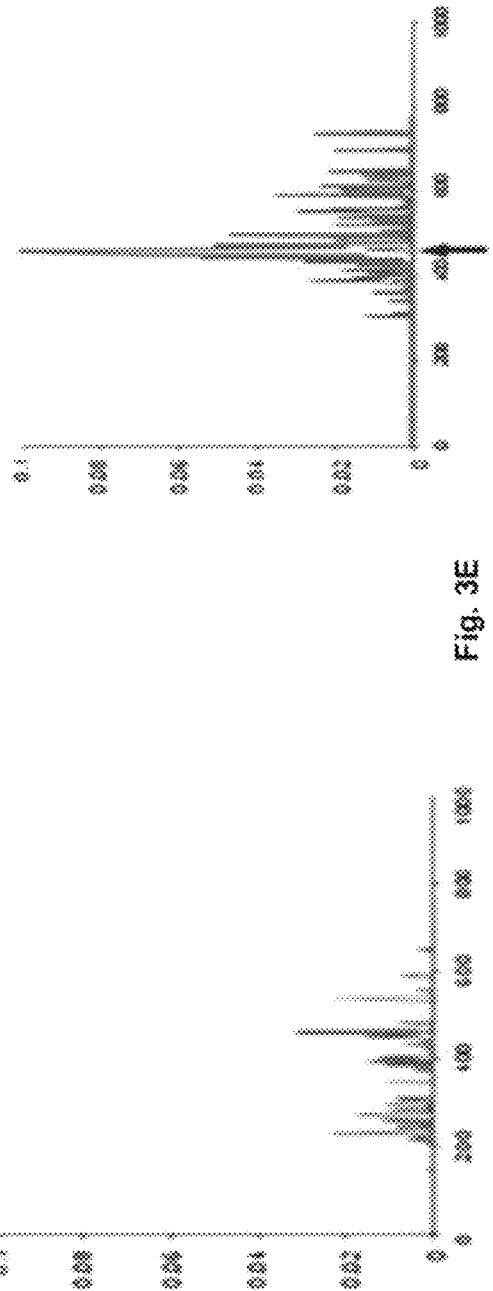
Figure 3F:
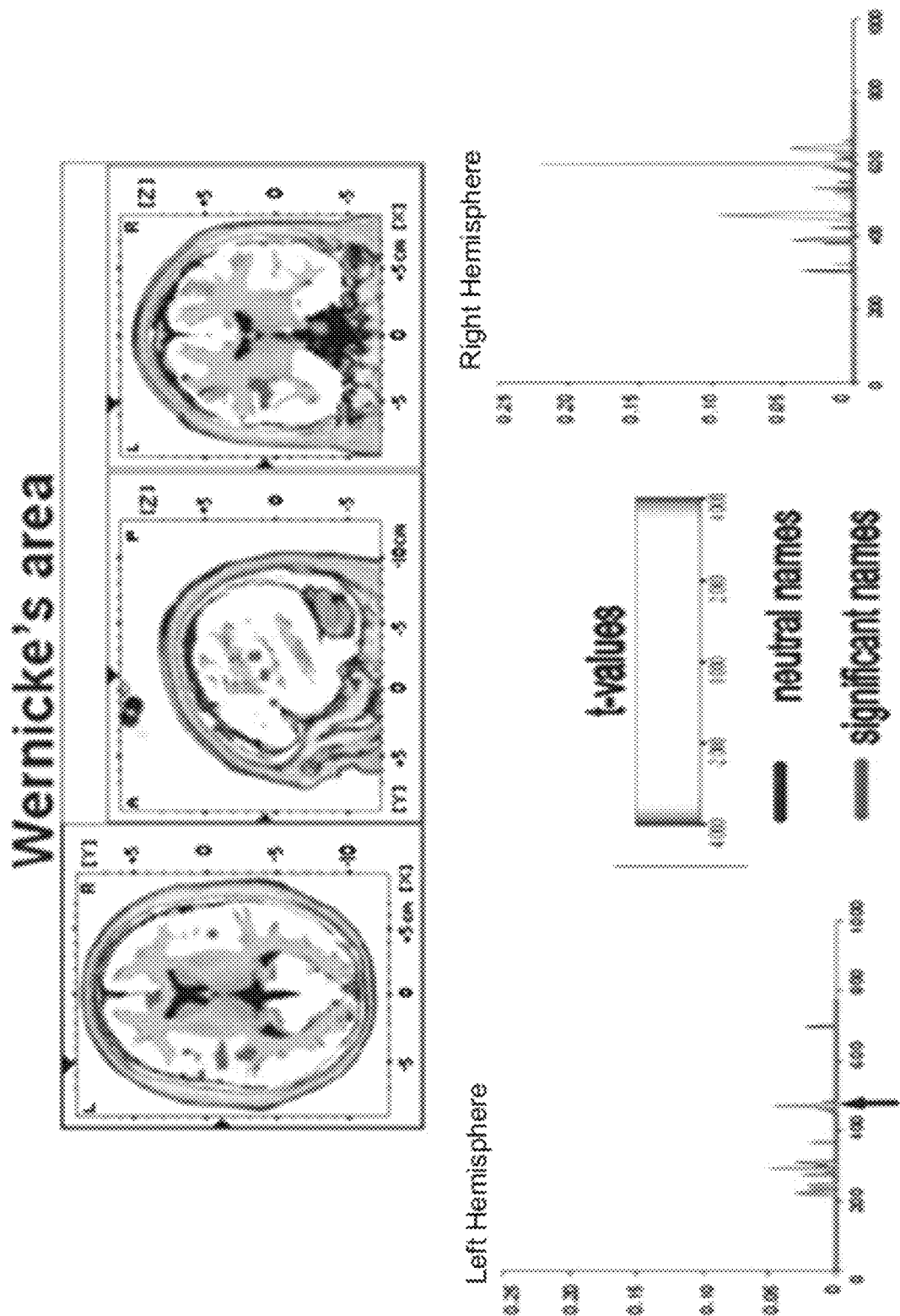
Figure 4A:
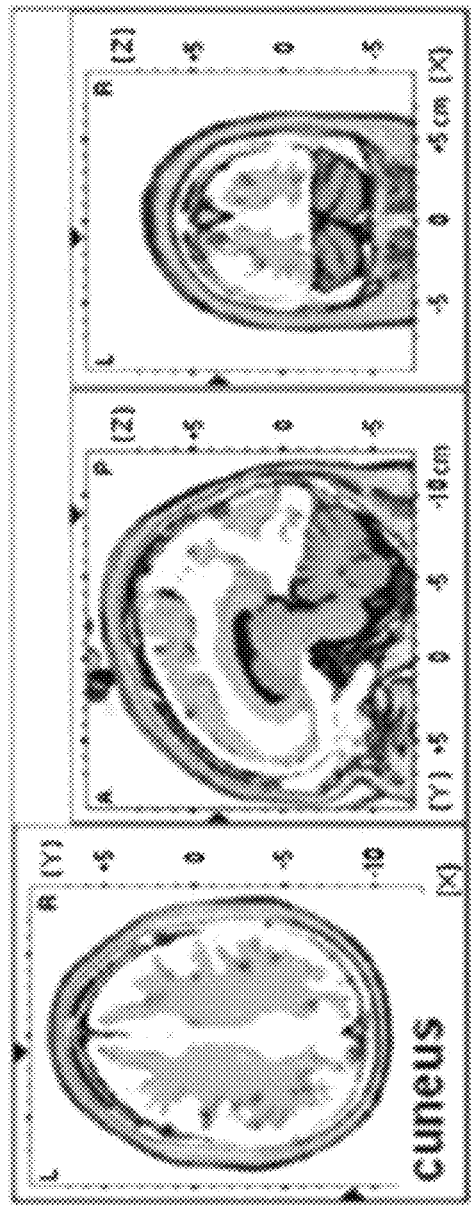
FIG. 4 shows the main cortical sources contributing to the difference in ERP components—results of a statistical comparison between subjectively significant and neutral names during several time periods. For each component, the vicinity of the area found to be most involved in the response is shown. On the right, the corresponding time period from which the sources were estimated is marked on the ERP waveform.
Figure 4A:
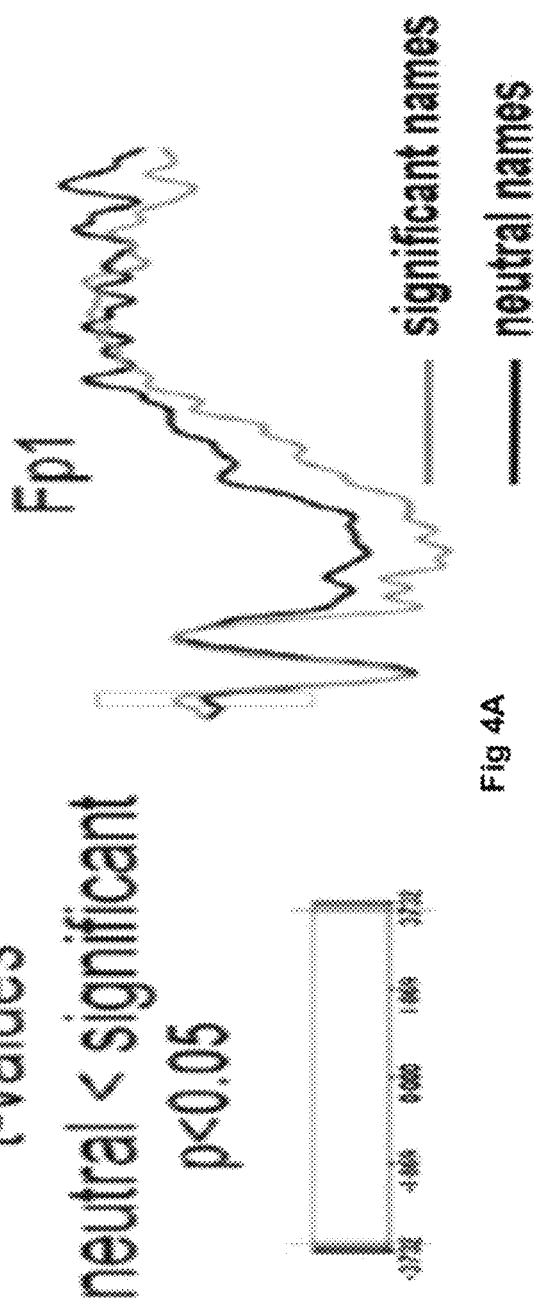
Figure 4B:
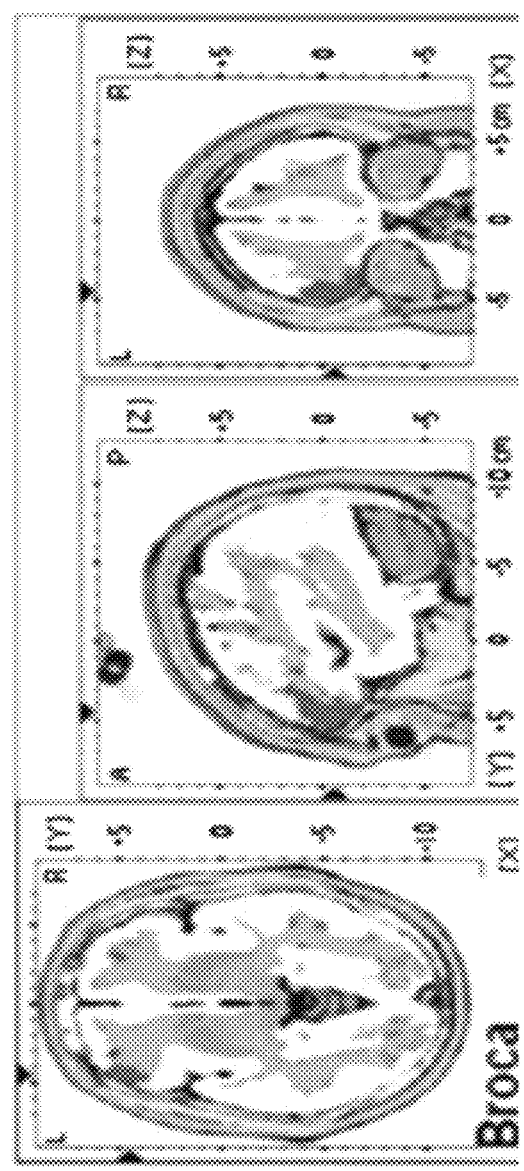
Figure 4B:
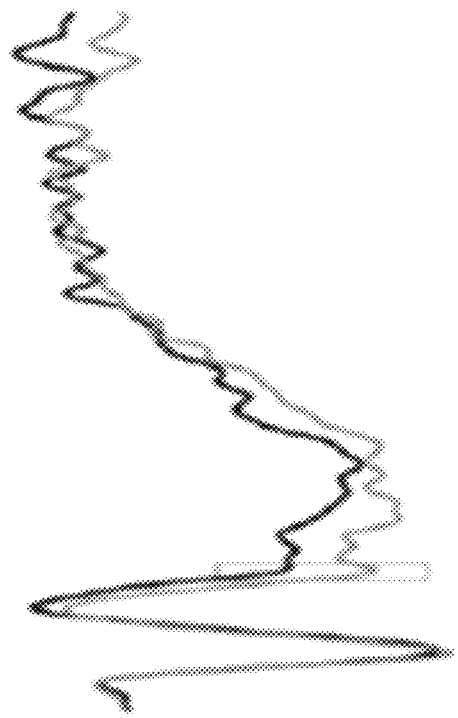
Figure 4C:
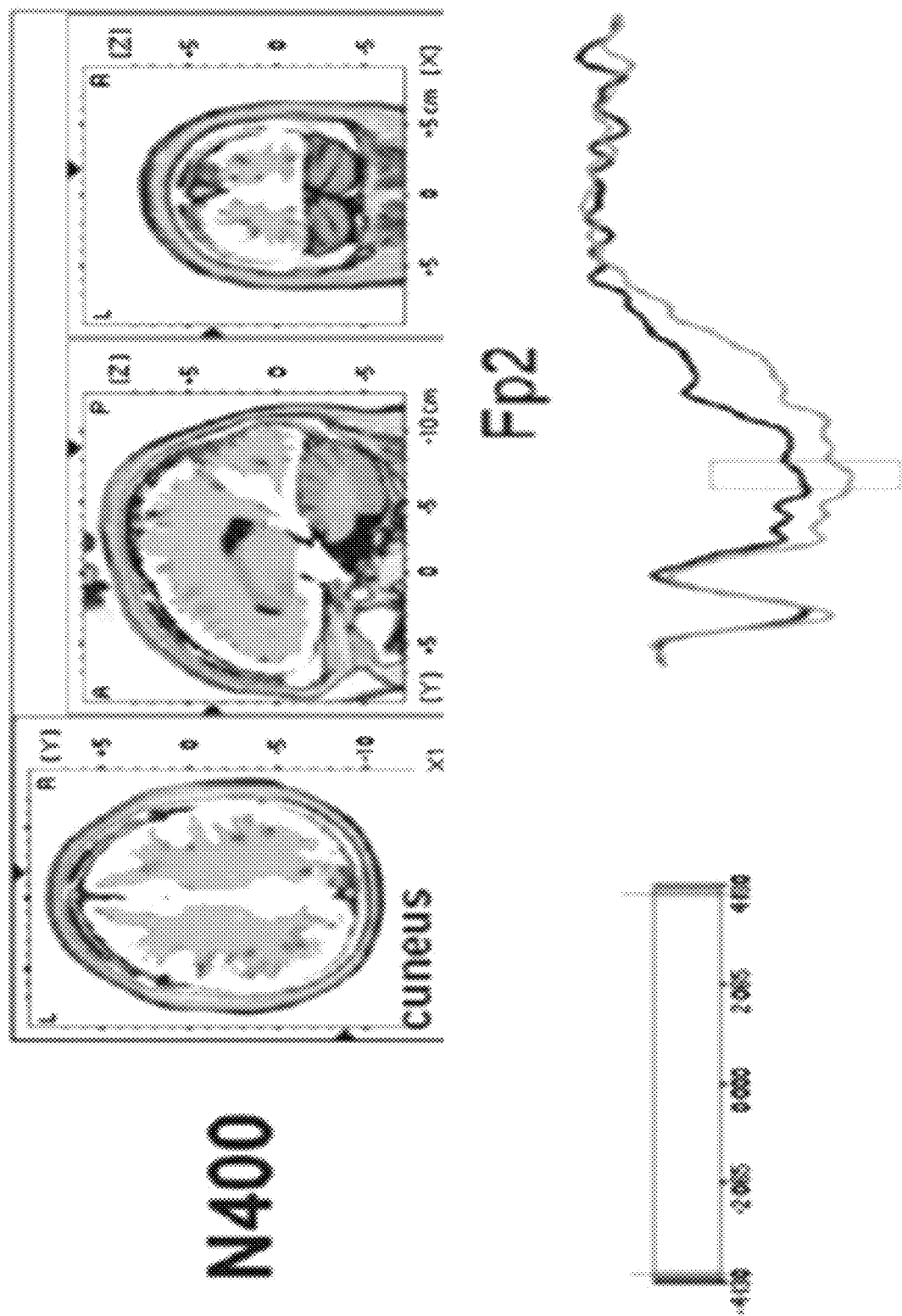
Figure 4D:
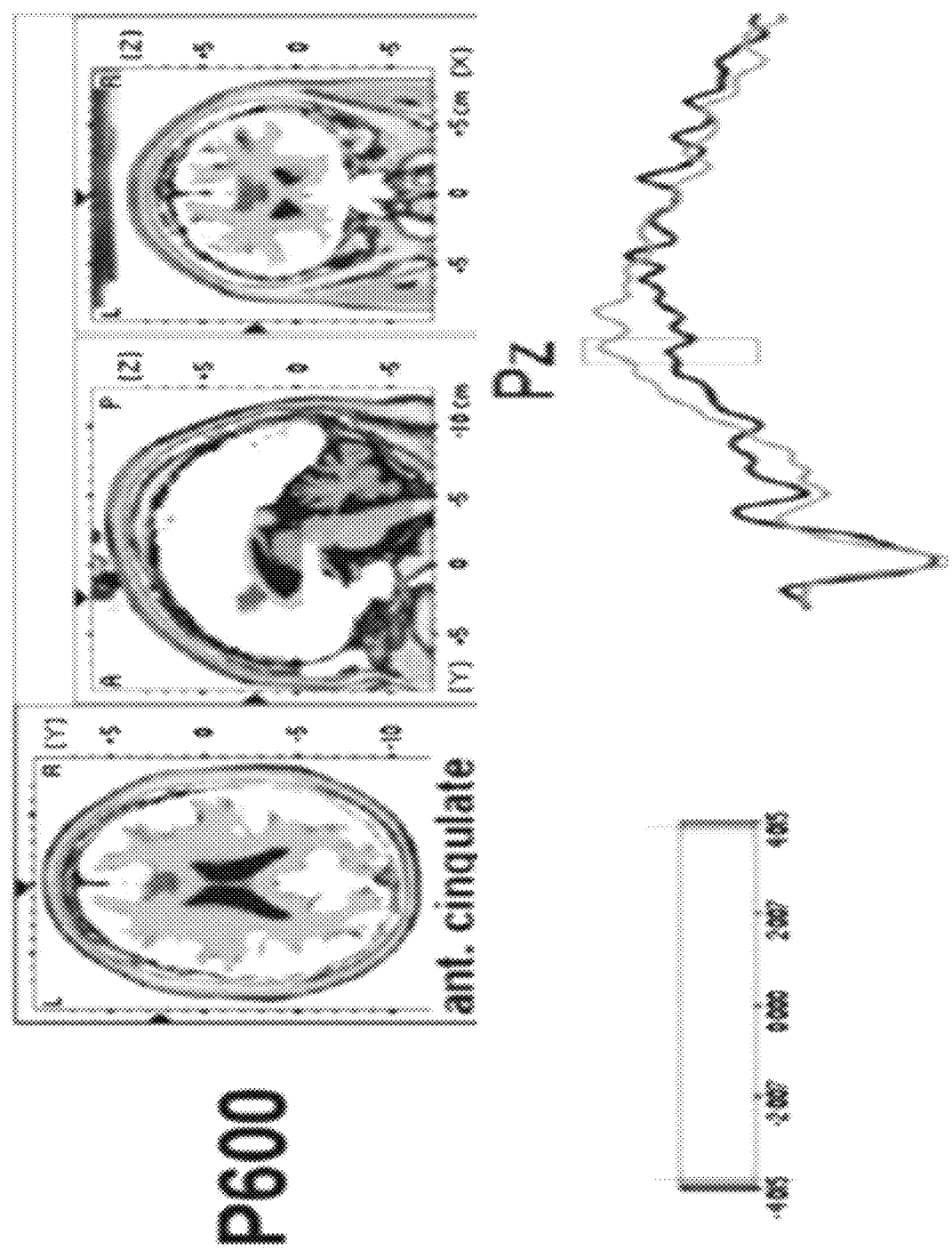

FIG. 2 presents bar graphs of the timing of activation in the vicinity of the main areas involved in the left and right hemispheres, demonstrating the more prevalent activation of left hemisphere structures in response to subjectively significant stimuli. Note the concurrent activation of the brain areas involved. FIG. 3 shows the level of brain activity in the vicinity of several areas in response to subjectively significant—compared to neutral stimuli. The graphs also show the comparable activation of homologous regions in both hemispheres. The areas detailed in the figures were the most significantly activated brain regions in the time period between 200 and 800 ms after stimulus onset. An overall enhanced brain activity was found in response to subjectively significant compared to neutral stimuli [$F(2,52)=12.39$; $P<0.005$]. Enhanced activation was found in response to both subjectively significant and neutral stimuli in the left hemisphere compared to the right hemisphere [$F(2,52)=12.55$; $P<0.005$]. A significant interaction between subjective significance and laterality was found [$F(2,52)=9.45$; $P<0.01$], with the subjective significance effect significantly more prominent in the left hemisphere. FIG. 4 summarizes activity in the vicinity of the main areas found to be specifically involved in the response to subjectively significant stimuli, when their activity was statistically compared to that of neutral stimuli, during peaks of activation in the ERP waveforms.

3. The Questionnaire

The questionnaire used in the experiment (see Appendix) intended to measure subjective significance to the subject of first names. Subjective significance (or subjective affective valence) of first names to the participant was defined as subjective significance of people in the participants' life that bear that name. Verbal stimuli in general have multiple dimensions (e.g., meaning, grammatical function, affective valence). In contrast, first names have only one major semantic dimension (subjective valence). The subjective meaning of a first name is mostly acquired from familiar people in the participants' life that bear this name. The questionnaire was developed in order to assess subjective significance of people in the participant's life.

The questionnaire was planned to target 3 dimensions of subjective significance: (1) General emotional significance; (2), Negative impact; and (3) recency of contact (closeness, past and present). Specific items were included to assess each of these factors. Questionnaire items were formulated to assess the following affective aspects: closeness, anger, liking, dislike, frustration, love, hatred. Additional items were included to assess duration and frequency of relationship. In addition, items targeted past traumatic experiences.

Although the questionnaire was originally developed to assess subjective significance of stimuli in the context of an event related brain potentials study, it can also serve other psychological and social studies of relationship and personality, beyond the realm of brain research. This questionnaire may also serve clinical practice, in mapping complicated relationships in the participant's life, assessing supporting relationships and characterizing relationships related to traumatic events in the participant's life.

The questionnaire, in its final form, included 46 yes\no and rating questions (see Appendix) on each name. The original questionnaire included 70 questions, and was reduced after the factor analysis. Each participant was questioned about all names in a list of 30 two syllable, common Hebrew names. Initially, the questionnaire included 70 items that were directed at 3 factors: (1) general emotional significance; (2) negative impact; and (3) recency of contact. Items were first formulated so that every factor that might affect the relationship between 2 people would be included and probed, with some redundant items asking about the same issues in different manners.

Emotional content questionnaires were addressed as well. Later, after a factor analysis, the detailed questionnaire was reduced to include only the most relevant and discriminating items. In rating answers, a positive answer indicated an emotionally loaded name, and the numerical value reflected magnitude.

Validation of the affective valence score was performed using a plethysmographic measure for sympathetic activation. Sympathetic activation is known to be affected by emotional response. The plethysmographic measurement was conducted on the same day as the interview, using a peripheral arterial tone (PAT) device. The PAT device [Itamar Medical; Caesarea, Israel] is a portable device based on the PAT signal. Finger pulse wave was measured by a plethysmographic technique (Bar, A.; Pillar, G.; Dvir, I.; Sheffy, J.; Schnall, R. P.; Lavie, P. Evaluation of a portable device based on peripheral arterial tone for unattended home sleep studies. Chest. 2003, 123(3):695-703; Dvir, I.; Adler, Y.; Freimark, D.; Lavie, P. Evidence for fractal correlation properties in variations of peripheral arterial tone during REM sleep. Am. J. Physiol. Heart. Circul. Physiol. 2002, 283(1):H434-9). The PAT signal was recorded while the participants were reclining in a comfortable armchair in an acoustically isolated chamber, listening to names (all 30 names in the list) presented by earphones. The participants were instructed to listen to the names and think about persons they knew bearing those names, without pressing any button. The interval between names was 20 seconds, to accommodate the slow time course and the known latency of the autonomic response (several seconds). Mean peak amplitude (MPA) was computed for 5 intervals of 3 seconds after each stimulus, using a baseline of 3 seconds before each stimulus onset, in order to track the minimal amplitude of PAT following the stimulus. The interval with the minimal MPA after the stimulus was chosen. PAT response was determined as the % of PAT signal change: [(minimum MPA after the stimulus−MPA at baseline)/MPA at baseline]×100. Those computations were conducted for the 3 most subjectively significant and 3 least subjectively significant names for each participant. ANOVA was performed to assess the effect of affective valence on the PAT response.

Informed consent was obtained. The questionnaire was filled in an oral interview. Each participant was asked the entire questionnaire about each person he knew bearing a name from the list of 30 common Hebrew names. For each name, the following procedure was repeated: Participant was asked to recall all the persons he knew, in the present and in the past, who bear that specific name. Then, participants were asked to specify their relationship with each person mentioned for that name (fellow student, a childhood friend, a family member, the bus driver, etc.). Participants were subsequently asked to shortly answer 70 questions about that person. Specific questions were included if the participant was, or was not in contact with that person at the time of interview. The questions were either dichotomic yes/no questions, or rating questions (rating between 1 and 5). In the rating questions, '1' meant "not at all", and '5' indicated "applies very much". Answers were marked by the interviewer. Items were scored so that higher scores mean higher subjective significance.

Rating values were transformed to dichotomous values by computing the average response for each participant on a given item across all questionnaires (across different persons' names) completed by that participant. Responses above that average were assigned a positive value, and those under—negative. In all, 455 questionnaires were completed and processed. Thus, most subjects rated more than one person for each name—in total 30-40 questionnaires were filled by each subject.

Factor analysis was conducted and internal consistency (for each factor) was measured. Internal consistency was assessed within each factor, between all the questions in this factor. Redundant, ambiguous, or low item-to-total correlation items were removed from the questionnaire and subsequently 46 of the original 70 items were included in the final Varimax rotation factor analysis.

Following the initial analysis, 46 of the original 70 items were found useful and were included in the questionnaire. The final items are presented in the Appendix.

Factor analysis demonstrated that a 3-factor solution best explained the variance in the responses to the questionnaire (98%). Factor 1 ("subjective significance"; 26 items) explained 54% of variance with loadings ranging from 0.76 to 0.43. Factor 2 ("negative connection"; 12 items) contributed an additional 25% of the explained variance with loadings ranging from 0.72 to 0.41, and factor 3 ("recency of contact"; 8 items) contributed 19% of the additional variance, with loadings ranging from 0.76 to 0.44. Table 1 lists the factor loadings for each item and Table 2 details the questions that were associated with each factor. When data were randomly halved, and factor analysis conducted separately for the two halves, the factor structure results were repeated.

All factors demonstrated good reliability (see Table 3). Factor 1 had a Cronbach's alpha of 0.94, while factor 2 was associated with an alpha of 0.88 and factor 3-0.82.

Validity of the subjective significance questionnaire was tested using an autonomic activation measure—the PAT signal. Correlation between the subjective significance score and the autonomic response measure was significant ($p<0.05$).

Enhanced autonomic response (reduced peak amplitude) was found after subjectively significant stimuli compared to neutral stimuli [$F(2,8)=10.12$, $p<0.05$]. Thus, subjective significance correlated well with high % change of the PAT signal.

APPENDIX

Following are the final 46 items of the questionnaire and their original numberings:

Factor 1:

Yes\No Questions

1. Would you prefer to see that person more frequently than you do at the present?
2. Do you see each other on your initiative more than once a week?
6. Has that person ever been the closest person (or the second closest) to you?
7. Has your acquaintance with that person affected your life?
9. Was your acquaintance with that person significant for you?
12. Is your acquaintance with that person still affecting you today?
13. Have you experienced significant events with that person?
15. Was that person present in any significant event you have experienced?
18. Has that person ever appeared in your dreams?
19. Have you ever felt closeness to that person?

Rating Questions (on a Scale of 1-5).

3. How much is this person in your life (Physically or not)? [Very much=5; not at all=1].
4. Rate the level of your closeness with that person. [Very much=5; not at all=1].
5. Rate the maximal level of closeness you have ever had with that person in the past [Very much=5; not at all=1].
8. Rate how much your acquaintance with that person affected your life [Very much=5; not at all=1].

10. Rate how significant your acquaintance with that person was to you [Very significant=5; not at all=1].
11. Rate how significant this person was to you at the time he was most significant for you. [Very significant=5; not at all=1].
14. Rate how intense the most intense experiences you have ever experienced with that person were. [Very intense=5; not at all=1].
17. Rate how often you find yourself thinking about this person. [Very often=5; not at all=1].
20. How often does this person come to your mind? [3 or more times a day=5; never=1]
21. How often do you think about this person? [All the time=5; never=1].
22. How significant is this person to you? [Very much=5; not at all=1].
23. How much has this person affected your life? [Very much=5; not at all=1].
24. How much do you like this person? [Very much=5; not at all=0].
25. What is the duration of your acquaintance? [All of my life=5; just one coincidental meeting=1].
26. How often do you see each other on your initiative? [Every day=5; never=1].

Factor 2:
Yes\No Questions
27. Would you prefer if you never met that person?
28. Has that person ever frustrated you?
30. Do you remember having any fights or quarrels with that person?
31. Has that person ever hurt you?
33. Have you ever hurt that person?
35. Have you ever hated that person?
36. Were you ever angry at that person?
Rating Questions (on a Scale of 1-5).
29. Rate how much frustration this person has ever caused you. [Very much=5; not at all=1].
32. Rate how much you were hurt by that person. [Very much=5; not at all=1].
34. Rate how much you have hurt that person. [Very much=5; not at all=1].
37. How often does this person make you nervous? [Very often=5; not at all=1].
38. How much do you dislike this person? [Very much=5; not at all=0].
39. In case you are not in contact with that person right now: rate how significant your acquaintance was at the time you were in contact. [Very significant=5; not at all=1].

Factor 3:
Yes/No Questions
40. Did the relationship end abruptly?
In case the participant doesn't see that person any more:
41. Has the relationship ended in a way you were not satisfied with, or in a traumatic way?
42. Do you remember your last meeting?
45. Has the relationship ended during the last 5 years?
46. Would you like to renew contacts with that person?
Rating Questions (on a Scale of 1-5).
43. In case you are not in contact right now—rate how intense your last meeting with that person was (if you can remember it). [Very intense=5; not at all=1].
44. In case you are not in contact right now—rate the intensity of your separation [very painful, I could not avoid thinking about this person all the time=5; I haven't even noticed the separation=1].

Although the invention has been described in detail, nevertheless changes and modifications, which do not depart from the teachings of the present invention, will be evident to those skilled in the art. Such changes and modifications are deemed to come within the purview of the present invention and the appended claims.

The invention claimed is:

1. A method of assessing a subjective significance of a given stimulus to a subject, said method comprising:
exposing the subject to a plurality of given stimuli;
during or after the exposing to the plurality of given stimuli, utilizing at least one electric sensor to detect brain activity within at least one brain area of the subject;
using a computer unit to receive detected brain activity patterns and analyzing the detected brain activity patterns;
comparing the detected brain activity patterns to an at least one reference pattern associated with a subjective significance stimulus brain responses of the subject, wherein the at least one reference pattern is characterized by brain activation patterns within areas on either hemisphere;
determining whether the at least one reference pattern is identified in the detected brain activity patterns responsive to a given stimulus of the plurality of given stimuli;
determining whether the given stimulus is subjectively significant to the subject based on the identifying of the at least one reference pattern in the detected brain activity patterns; and
comparing detected brain activity patterns responsive to different stimuli to each other, wherein a first stimulus that induces a stronger brain activation than a second stimulus is identified as being more subjectively significant than the second stimulus.

2. The method according to claim 1, wherein areas on either hemisphere are selected from the group consisting of:
middle frontal gyrus, superior frontal gyrus, anterior cingulate gyrus, medial frontal gyrus, posterior cingulate gyrus, Broca's area, superior temporal gyrus, Wernicke's area, Wernicke's homologous area on the right hemisphere, supramarginal gyrus, postcentral gyrus, orbital gyrus, middle temporal gyrus, inferior temporal gyrus, precentral gyrus, inferior parietal lobule, superior parietal lobule, precuneus, postcentral gyrus, hippocampus, insula, inferior frontal gyrus, and cuneus.

3. The method according to claim 2, wherein detected brain activity patterns responsive to different stimuli are compared to each other and a first stimulus that induces brain activation in a larger number of brain areas than a second stimulus is identified as being more subjectively significant than the second stimulus.

4. The method according to claim 2, wherein the at least one reference pattern is characterized by brain activation within one or more of the brain areas and brain tissue in proximity thereto around a time of a P1 component in an event related potential (ERP) response to said given stimulus or at a timeframe around 0 to 150 milliseconds from stimulus onset, wherein P1 is measured and determined as a first ongoing positive deflection from stimulus onset over prefrontal scalp locations by one or more electrodes on prefrontal scalp locations.

5. The method according to claim 2, wherein the at least one reference pattern is characterized by brain activation within one or more brain areas and brain tissue in proximity thereto around a time of an N2 event related potential component in an event related potential response to the given stimulus or around a timeframe of 0 to 600 milliseconds from stimulus onset, wherein N2 is measured and determined as a second ongoing prominent negative deflection from stimulus onset over frontal or central scalp locations and is measured by one or more electrodes selected from the group consisting of: F3; Fz; F4; C3; Cz; C4, and similar electrodes on central or frontal scalp locations as defined according to the 10/20 system of electrodes or a similar system of electrodes.

6. The method according to claim 2, wherein the at least one reference pattern is characterized by brain activation within one or more brain areas and brain tissue in proximity thereto around a time of an N400 event related potentials component in an event related potentials response to the given stimulus in said person or around a timeframe of 100 to 700 milliseconds from stimulus onset wherein N400 is measured and determined as a maximal negative deflection at a time 200 to 600 milliseconds from stimulus onset over a frontal or prefrontal scalp location and is measured by one or more electrodes selected from the group consisting of: Fp1; Fp2, and similar electrodes on frontal or prefrontal scalp locations according to the 10/20 system of electrodes or a similar system of electrodes.

7. The method according to claim 2, wherein the at least one reference pattern is characterized by brain activation within one or more of the brain areas and brain tissue in proximity thereto around a time of a P600 event related potential component in an event related potentials response to the given stimulus in said person or around a timeframe of 200 to 1400 milliseconds from stimulus onset wherein P600 is measured and determined as the maximal positive deflection at a time 200 to 1400 milliseconds from stimulus onset over parietal scalp locations and is measured by one or more electrodes selected from the group consisting of:
P3; Pz; P4, and similar electrodes on parietal scalp locations according to the 10/20 system of electrodes or a similar system of electrodes.

8. The method according to claim 2, wherein the at least one reference pattern is characterized by brain activation within one or more brain areas and brain tissue in proximity thereto with one or more peaks in their activation at a time after stimulus onset.

9. The method according to claim 2, wherein the at least one reference pattern is characterized by brain activation within one or more brain areas and brain tissue in proximity thereto at 600 milliseconds or later after stimulus onset.

10. The method according to claim 1, wherein the at least one reference pattern is characterized by brain activation within areas on either hemisphere selected from a group consisting of: medial frontal gyrus, superior frontal gyrus, Broca's area, middle frontal gyrus, superior temporal gyrus, Wernicke's area, Wernicke's homologous area on the right hemisphere, and brain tissue in proximity thereto.

11. The method according to claim 1, wherein detected brain activity patterns are comprised of electroencephalogram (EEG) signals.

12. The method according to claim 11, wherein detected brain activity patterns are comprised of EEG signals are processed to extract event related potentials (ERP) responses to the given stimulus.

13. The method according to claim 12, wherein ERP responses to different stimuli are compared to each other, and stimuli to which there is a relatively greater amplitude of at least one certain event related potentials component are identified as more subjectively significant to said subject than other stimuli.

14. The method according to claim 13, wherein the at least one certain event related potentials component is selected from a group consisting of: P1, N2, N400, and P600 ERP components, wherein P1 is measured and determined as a first ongoing positive deflection from stimulus onset over prefrontal scalp locations measured by one or more electrodes on a prefrontal scalp location and N2 is measured and determined as a second ongoing prominent negative deflection from stimulus onset over a frontal or central scalp location measured by one or more electrodes selected from a group consisting of: F3; Fz; F4; C3; Cz; C4, and similar electrodes on frontal or central scalp locations as stated by the 10/20 system of electrodes or a similar system of electrodes and N400 is measured and determined as a maximal negative deflection at a time 200 to 600 milliseconds from stimulus onset over frontal or prefrontal scalp locations measured by one or more electrodes selected from the group consisting of: Fp1; Fp2, and similar electrodes on frontal or prefrontal scalp locations as stated by the 10/20 system of electrodes or a similar system of electrodes and P600 is measured and determined as a maximal positive deflection at a time 200 to 1400 milliseconds from stimulus onset over parietal scalp locations as measured by one or more electrodes selected from a group consisting of: P3, Pz, P4, and similar electrodes on parietal scalp locations as stated by the 10/20 system of electrodes or a similar system of electrodes.

15. The method according to claim 12, wherein ERP responses to different stimuli are compared to each other and stimuli to which there is a shorter latency of at least one certain event related potentials component are identified as more subjectively significant to said subject than other stimuli.

16. The method according to claim 15, wherein the at least one certain event related potentials component is selected from a group consisting of: P1, N2, N400, and P600 ERP components, wherein P1 is measured and determined as a first ongoing positive deflection from stimulus onset over prefrontal scalp locations measured by one or more electrodes on a prefrontal scalp location and N2 is measured and determined as a second ongoing prominent negative deflection from stimulus onset over a frontal or central scalp locations measured by one or more electrodes selected from a group consisting of: F3; Fz; F4; C3; Cz; C4, and similar electrodes on frontal or central scalp locations as stated by the 10/20 system of electrodes or a similar system of electrodes and N400 is measured and determined as a maximal negative deflection at a time 200 to 600 milliseconds from stimulus onset over frontal or prefrontal scalp locations measured by one or more electrodes selected from the group consisting of: Fp1; Fp2, and similar electrodes on frontal or prefrontal scalp locations as stated by the 10/20 system of electrodes or a similar system of electrodes and P600 is measured and determined as a maximal positive deflection at a time 200 to 1400 milliseconds from stimulus onset over parietal scalp locations as measured by one or more electrodes selected from a group consisting of: P3, Pz, P4, and similar electrodes on parietal scalp locations as stated by the 10/20 system of electrodes or a similar system of electrodes.

17. The method according to claim 2, wherein detected brain activity patterns responsive to different stimuli are compared to each other and an averaged measure of brain activation is determined and a first stimulus that induces a stronger brain activation than the averaged measure in certain brain areas is identified as being more subjectively significant than other stimuli inducing brain activation lesser than the averaged measure.

18. The method according to claim 2, wherein detected brain activity patterns responsive to different stimuli are compared to each other and a first stimulus that induces brain activation in a larger number of brain areas than an averaged number of brain areas involved for different stimuli is identified as being more subjectively significant than other stimuli inducing activation in a lesser number of brain areas.

\* \* \* \* \*